(12) United States Patent
Nakajima et al.

(10) Patent No.: US 7,960,154 B1
(45) Date of Patent: Jun. 14, 2011

(54) POLYESTER-BASED-PLASTIC-DEGRADING BACTERIA, POLYESTER-BASED-PLASTIC-DEGRADING ENZYMES AND POLYNUCLEOTIDES ENCODING THE ENZYMES

(75) Inventors: Toshiaki Nakajima, Tsukuba (JP); Yukie Shigeno, Tsukuba (JP)

(73) Assignee: Japan Science and Technology Agency, Kawaguchi-Shi (JP)

( * ) Notice: Subject to any disclaimer, the term of this patent is extended or adjusted under 35 U.S.C. 154(b) by 361 days.

(21) Appl. No.: 11/795,578

(22) PCT Filed: Jan. 23, 2006

(86) PCT No.: PCT/JP2006/000942
§ 371 (c)(1),
(2), (4) Date: Dec. 18, 2007

(87) PCT Pub. No.: WO2006/078011
PCT Pub. Date: Jul. 27, 2006

(30) Foreign Application Priority Data

Jan. 21, 2005 (JP) ................................ 2005-014744
Jan. 21, 2005 (JP) ................................ 2005-014761

(51) Int. Cl.
*C12N 9/00* (2006.01)
*C12N 1/20* (2006.01)
*C12N 15/00* (2006.01)
*C07H 21/04* (2006.01)

(52) U.S. Cl. .................. 435/183; 435/252.3; 435/320.1; 536/23.2

(58) Field of Classification Search .................. None
See application file for complete search history.

(56) References Cited

U.S. PATENT DOCUMENTS 6,066,492 A * 5/2000 Tokiwa et al. ............. 435/253.5

FOREIGN PATENT DOCUMENTS

| JP | 2001-261506 A | 9/2001 |
|---|---|---|
| JP | 2004-166540 A | 6/2004 |
| JP | 2004-166542 A | 6/2004 |
| JP | 2004-261102 A | 9/2004 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Akutsu-Shigeno et al., "Microbial degradation of polyurethanes; The peculiarity of solid-plastic-degrading enzyme," Bioscience & Industry, vol. 60, No. 3, 2002, pp. 153-158.
Takakuchi et al., "Properties of plastics degrading enzyme derived from *Laptothrix* sp. 3A, Kabu Yurai Plastic Bunkai Koso no Shoseishitsu," The Society for Biotechnology, Japan Taikai Koen Yoshishu, vol. 2005, 2005, pp. 106.
Uchida et al., "Properties of a bacterium which degrades solid poly(tetramethylene succinate)-co-adipate, a biodegradable plastic," FEMS Microbiol. Lett, vol. 189, 2000, pp. 25-29.
Extended European Search Report dated May 8, 2009 for corresponding European application No. 06712158.
"*Aspergillus oryzae* AoaxeA gene for acetyl xylan esterase, complete cds", Database Embl, Mar. 19, 2004, XP-002524411.
Akutsu-Shigeno et al., Applied and Environmental Microbiology, May 2003, vol. 69, No. 5, pp. 2498-2504.
Teeraphatpornchai et al., Biotechnology Letters, vol. 25, 2003, pp. 23-28.
Uchida et al., Journal of Bioscience and Bioengineering, vol. 93, No. 2, 2002, pp. 245-247.
Nomura et al., Journal of Fermentation and Bioengineering, vol. 86, No. 4, 1998, pp. 339-345.
Akutsu et al., Applied and Environmental Microbiology, Jan. 1998, vol. 64, No. 1, pp. 62-67.
Nakajima-Kambe et al., FEMS Microbiology Letters, vol. 129, 1995, pp. 39-42.

* cited by examiner

*Primary Examiner* — Christian L Fronda
(74) *Attorney, Agent, or Firm* — Birch, Stewart, Kolasch & Birch, LLP

(57) ABSTRACT

The present invention relates to a novel microorganism and a method for degrading plastics or for collecting monomers through biological treatment using the microorganism. The present invention also relates to a novel polyester-based plastic-degrading enzyme and a polynucleotide encoding the enzyme, as well as a method for degrading plastics or for collecting monomers using the enzyme or a microorganism expressing the enzyme.

24 Claims, 8 Drawing Sheets

[Figure 1]
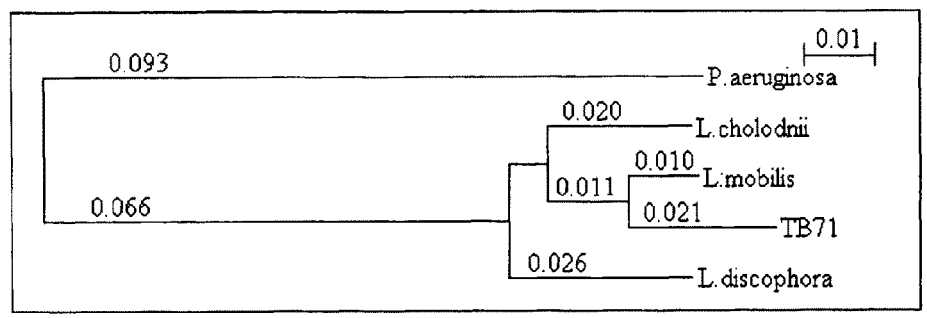

[Figure 2]
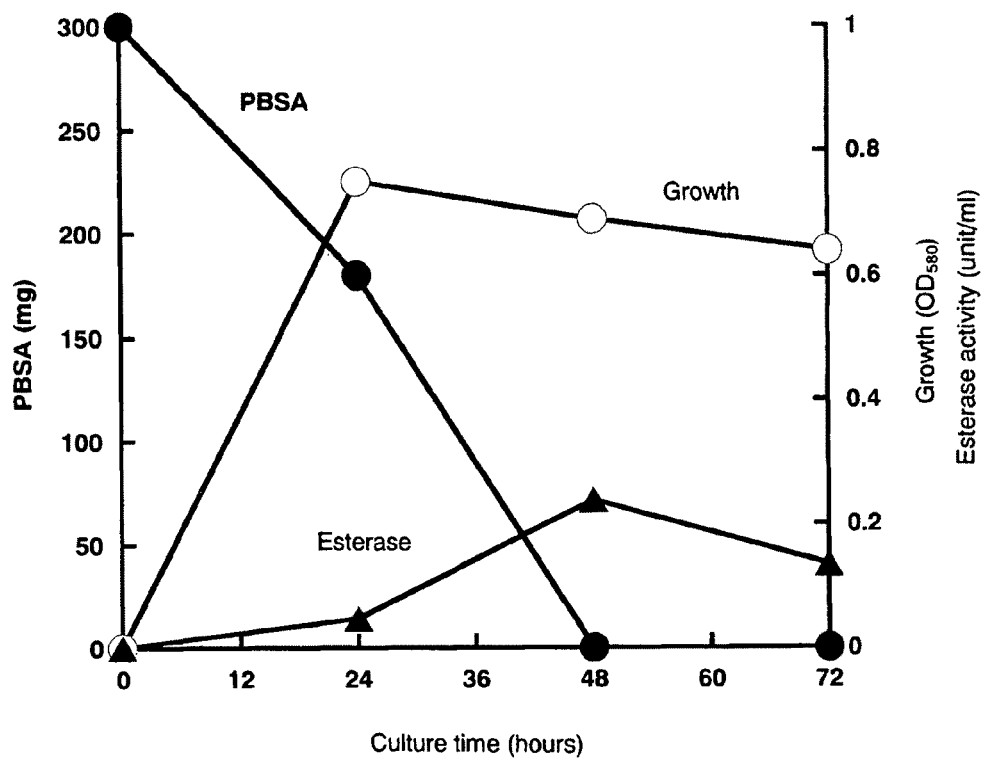

[Figure 3]
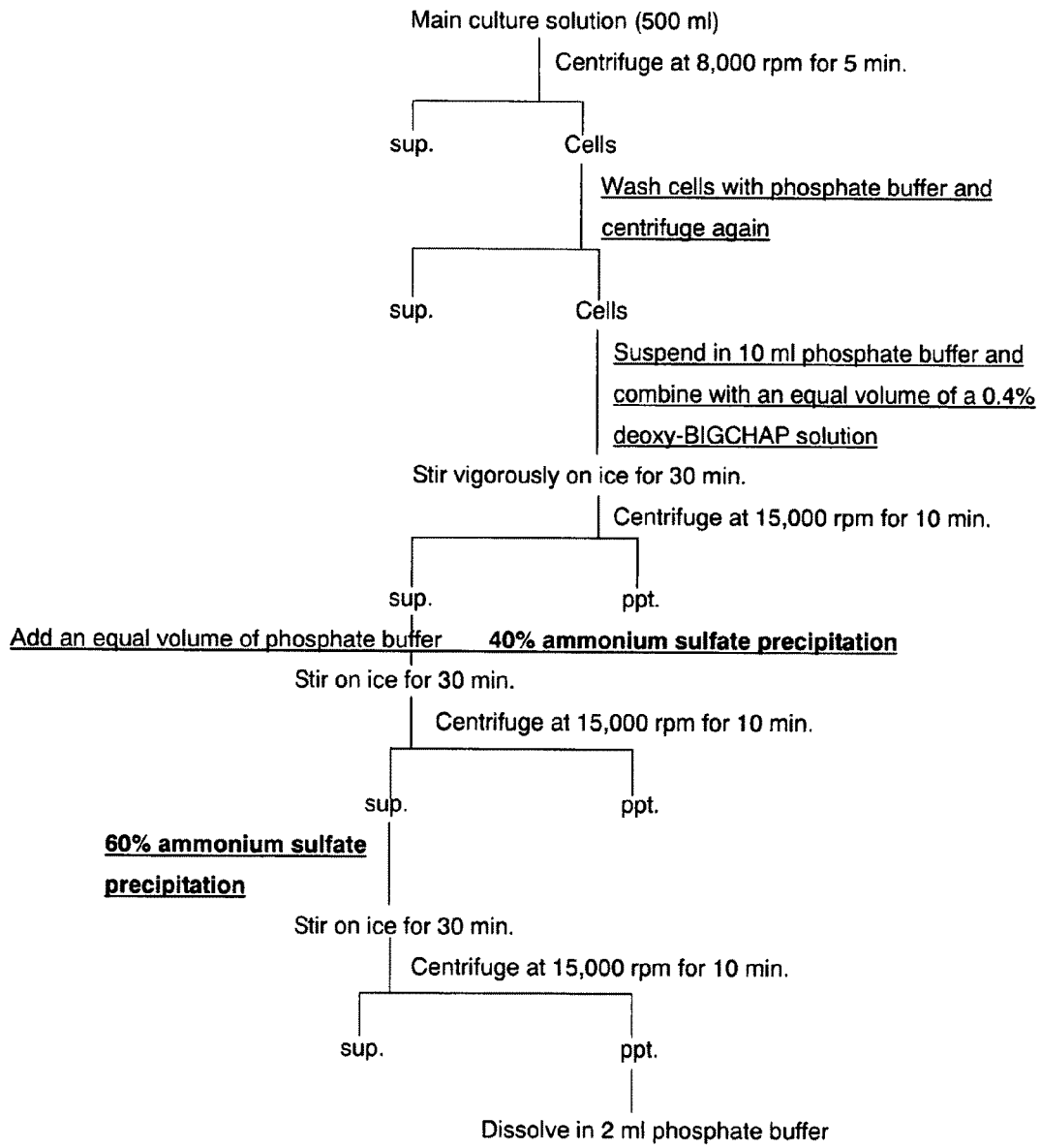

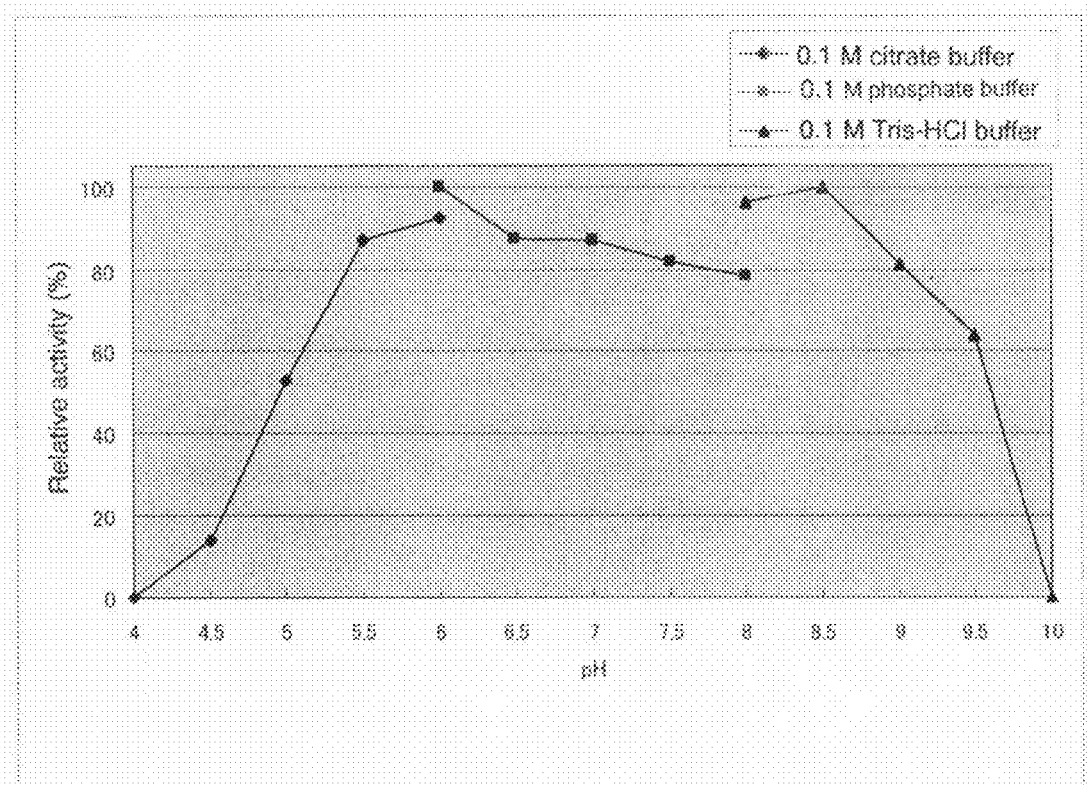
[Figure 4]

[Figure 5]
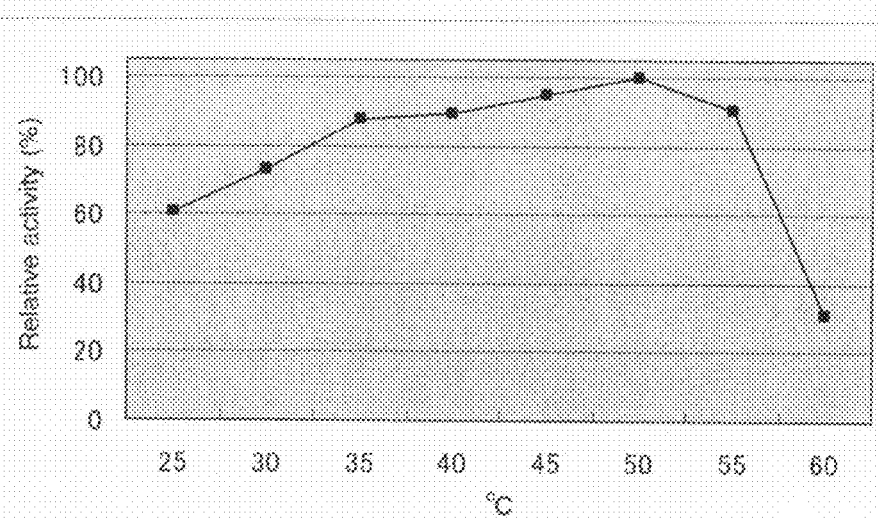
[Figure 6]
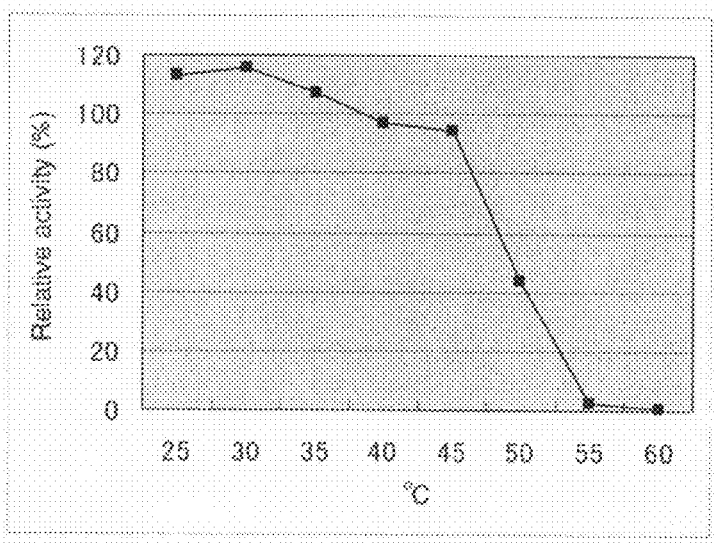

[Figure 7]
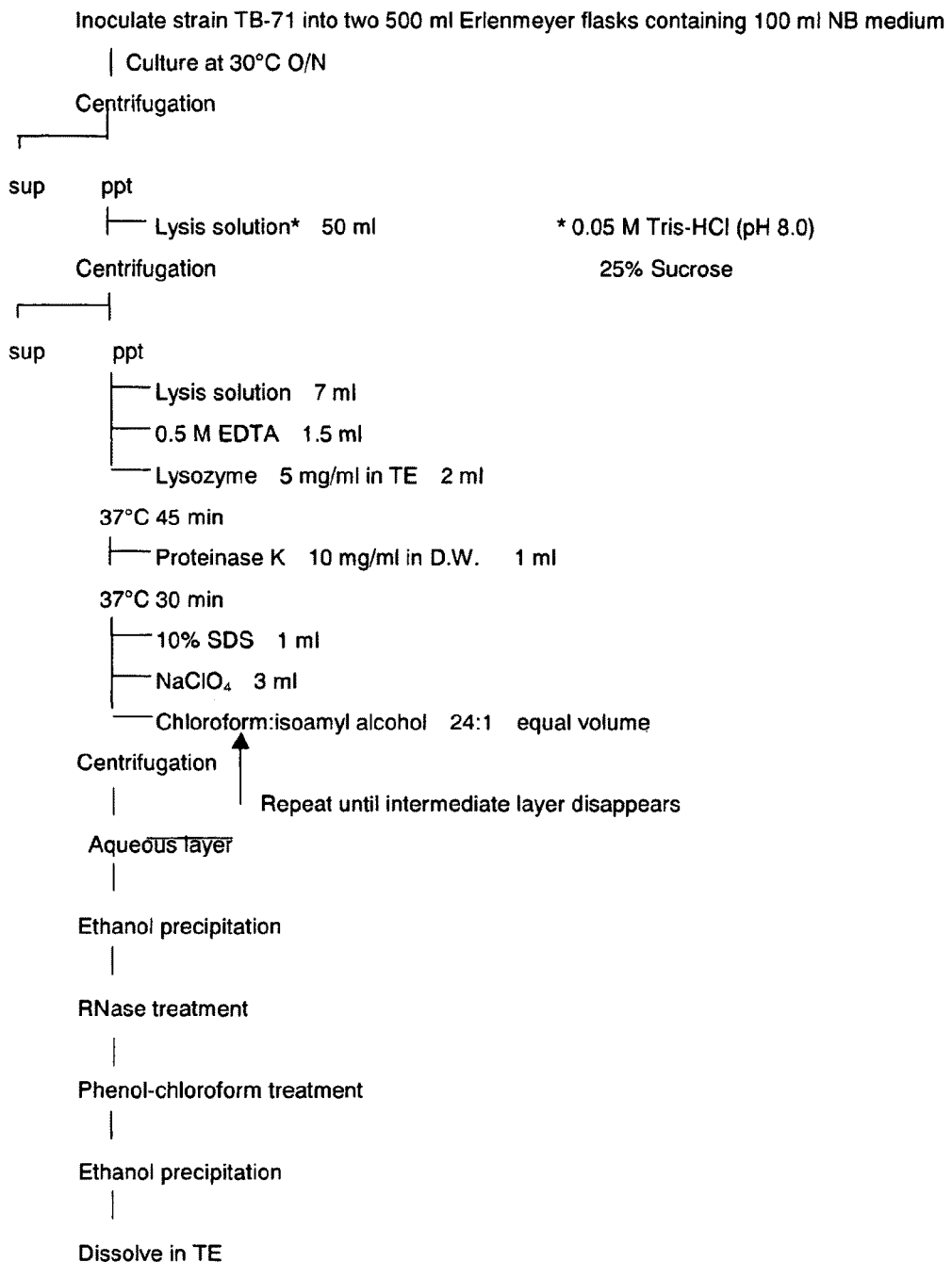

[Figure 8]
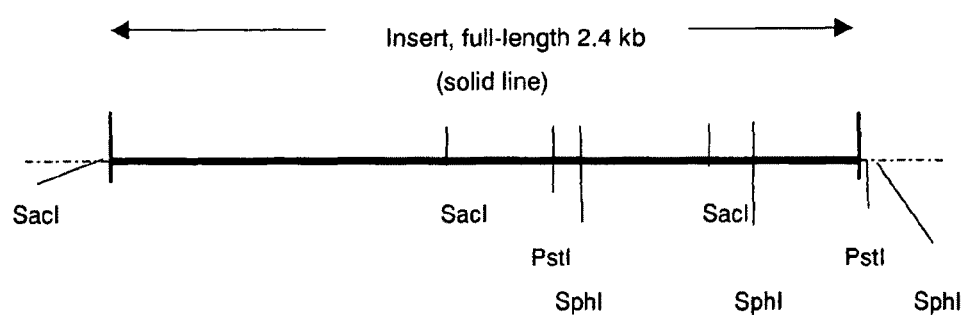
[Figure 9]
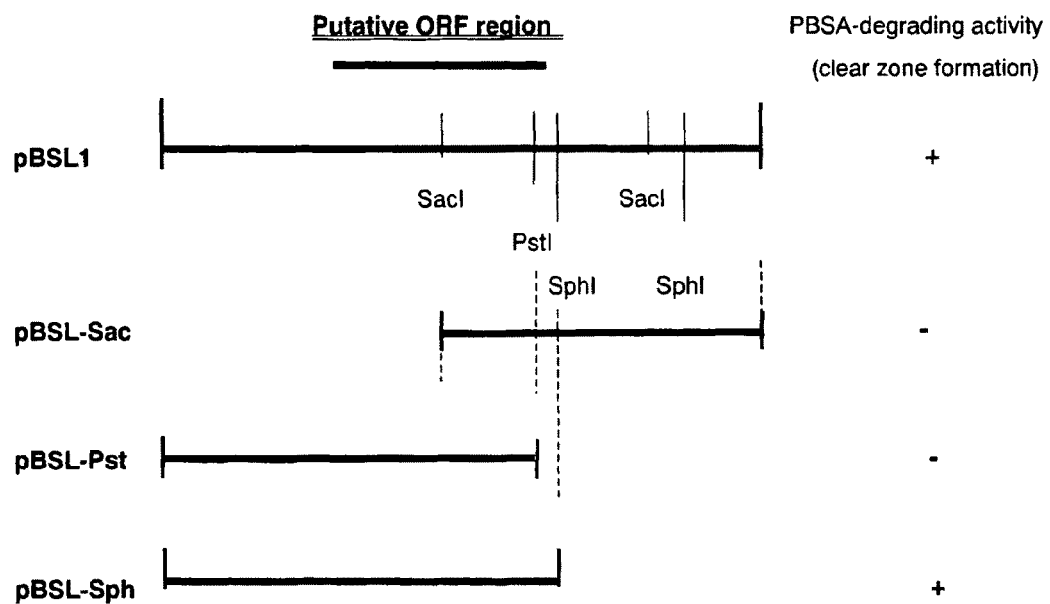

[Figure 10]

MQRRLIQRLAFLAATTVFAGSAFAGNFTASYSAGLSSYSIKGTEPDSGKHPVFIYTVGTTESYDNA
QAMGAVAEMAAKGFVAAAVQYDSSLFGTCSQILSKARYIYNSGSTSSAISKLCSRASADCSKGVV
VAGFSQGSVIALNAKNYDSRVRAAYGMGSHTSYTTYLMSSCMTPGGYTISKDNVRIVNGQSDSFP
VGTVRSSSESVAGRSCGSFAYECLATNGSGWIMIRDSDVGDLSADHCYQRVGGCTGLQSVTDST
WRNGSTNWGLKANLNWLNGFVTH

[Figure 11]

ATGCAACGACGCCTGATCCAGCGCCTGGCCTTCCTGGCCGCCACCACCGTCTTCGC
CGGCAGCGCCTTCGCCGGCAACTTCACGGCCAGCTACAGCGCCGGCCTGAGCAGCT
ACAGCATCAAGGGCACCGAGCCCGACTCGGGCAAGCACCCGGTGTTCATCTACACC
GTGGGCACCACCGAGAGCTACGACAACGCCCAGGCCATGGGCGCCGTGGCCGAGA
TGGCCGCCAAGGGCTTCGTCGCCGCCGCCGTGCAGTACGACAGCAGCCTGTTCGGC
ACCTGCTCGCAGATCCTGTCCAAGGCGCGCTACATCTACAACAGCGGCTCCACCAGC
AGCGCCATCTCGAAGCTGTGCTCGCGCGCCAGCGCCGACTGCTCCAAGGGCGTGGT
CGTCGCCGGCTTCAGCCAGGGCTCGGTGATCGCCCTCAACGCCAAGAACTACGACA
GCCGCGTGCGTGCCGCCTACGGCATGGGCTCGCACACGTCGTACACGACCTACCTG
ATGAGCTCGTGCATGACGCCGGGCGGCTACACGATCTCGAAGGACAACGTGCGCAT
CGTCAACGGCCAGAGCGACAGCTTCCCGGTCGGCACCGTGCGCTCGTCGTCCGAGT
CGGTCGCCGGCCGCAGCTGCGGCTCGTTCGCCTACGAATGCCTGGCCACCAACGG
CAGCGGCTGGATCATGATCCGCGACAGCGACGTGGGCGACCTCTCGGCCGACCACT
GCTACCAGCGCGTGGGCGGCTGCACCGGCCTGCAGAGCGTGACCGACAGCACCTG
GCGCAACGGCTCCACCAACTGGGGCCTGAAGGCCAACCTGAACTGGCTCAACGGCT
TCGTCACCCAC

POLYESTER-BASED-PLASTIC-DEGRADING BACTERIA, POLYESTER-BASED-PLASTIC-DEGRADING ENZYMES AND POLYNUCLEOTIDES ENCODING THE ENZYMES

TECHNICAL FIELD

The present invention relates to a novel microorganism and a method for degrading plastics or for collecting monomers through biological treatment using the microorganism. The present invention further relates to a novel polyester-based-plastic-degrading enzyme and a polynucleotide encoding the enzyme, as well as a method for degrading plastics or for collecting monomers using the enzyme or a microorganism expressing the enzyme.

BACKGROUND ART

In light of global environmental protection, the recent most important issue is to construct circulating social systems that can be maintained and continued. In such a social situation, much effort has also been made to develop recycling techniques for plastic wastes. Recycling techniques for plastic wastes are divided into two major types: physical approach (thermal recycling, material recycling) and chemical approach (chemical recycling). Among them, the former physical treatment has already been made practical for PET or other resins on a commercial basis because it is relatively simple and cost-effective. However, this approach cannot avoid quality loss due to repeated use and hence the resulting recycled products will have limited applications.

In the case of chemical recycling, on the other hand, waste plastics are chemically degraded into monomers or oligomers, which are then collected and used as source materials for resynthesis of new plastics. This approach allows production of plastic products completely comparable to primary products, and causes no quality loss. In light of these facts, products with chemical recycling in mind have recently been developed and a part of them has already been on the market.

Moreover, chemical recycling is also effective as a treatment technique for biodegradable plastics which have been spreading rapidly in recent years. In the future, biodegradable plastics will constitute nearly half of the total yield of plastics, and it is also expected that attention will be given to the development of efficient techniques for their recycling in the future. Biodegradable plastics currently in circulation are almost exclusively polyester-based plastics. This means that monomer recycling can be very easily achieved for these plastics because their monomer components such as organic acids and polyhydric alcohols are joined via ester bonds sensitive to hydrolysis.

However, a large problem arises when actually attempting recycling because wastes comprise multiple types of materials in admixture. Although there is a cry for separated collection of wastes, it will actually be impossible to completely achieve separated collection when taking into account the awareness of people who discard wastes as well as the time and effort required for separated collection. In particular, plastic products generally use a plurality of different plastics in combination, and currently used techniques do not enable the separation of all plastic wastes according to plastic types. For this reason, under present circumstances, recycling is limited to wastes which are easy to separate and collect, regardless of recycling techniques.

Likewise, the chemical recycling of biodegradable plastics is also very disadvantageous in terms of costs because standard chemical degradation such as acid or alkali degradation produces monomers in a mixture form, which require many processes for their purification.

To overcome this problem, a new process has been proposed in which enzymes are used for chemical recycling of plastics. As to merits resulting from the use of enzymes, the substrate specificity of enzymes may be the most excellent feature although it is also important in that reactions can be carried out at normal temperature and under normal pressure, thereby saving energy costs and requiring no organic solvent responsible for environmental pollution. In general, enzymes have substrate specificity and clearly select their target substrates. Thus, a combination of enzymes, each being reactive to only a certain specific plastic, allows efficient extraction of high purity monomers from plastic wastes in a mixture form, without requiring any separation process. In general, bioprocesses require high costs and hence are disadvantageous in this point without any doubt, but it is a great merit to achieve extraction of high purity monomers without separation. Particularly, also in view of the fact that biodegradable plastics are degraded by the action of enzymes secreted by microorganisms in the natural world, it can be expected to develop a process using enzymes derived from such degrading bacteria.

To establish enzymatic recycling, the premise is the presence of a strong plastic-degrading enzyme having high substrate specificity. In particular, since plastic wastes are practically discarded in solid form such as chips and/or blocks, bacteria which degrade solids are particularly important.

Enzymes previously known for their ability to degrade polyester-based solid plastics include enzymes that degrade polyhydroxyalkanoate (PHA), i.e., PHA depolymerases. PHA is a natural polyester produced by microorganisms and has been used as a biodegradable plastic from a long time ago. Since PHA is an energy storage substance inherent to bacteria, there is of course a metabolic system where PHA is degraded to produce energy. Thus, many bacteria including *Pseudomonas* spp. are known to have the ability to degrade PHA. On the other hand, however, such enzymes have little reactivity to any polyester-based plastic other than PHA.

Examples known as enzymes derived from unnatural plastic-degrading bacteria are those capable of degrading ester-based polyurethanes. Such enzymes are derived from *Comamonas acidovorans* and cleave ester bonds in ester-based solid polyurethanes to produce water-soluble monomers [Akutsu, Y., Nakajima-Kambe, T., Nomura, N., and Nakahara, T.: Purification and properties of a polyester polyurethane-degrading enzyme from *Comamonas acidovorans* TB-35. Appl. Environ. Microbiol., 64, 62-67 (1998); and JP 09-224664 A entitled "Method for polyurethane esterase purification and method for ester-based polyurethane degradation" (Applicant: Suzuki Motor Corporation; Inventors: Toshiaki Nakajima, et al.)].

Other polyester-based plastics include polylactic acid, polybutylenesuccinate (PBS), polybutylenesuccinate-co-adipate (PBSA) and polycaprolactone (PCL), each of which is a biodegradable plastic. Although there have been many reports of degrading bacteria for these biodegradable plastics, most of these reports were directed to degradation of emulsified or powdered plastics or thin films of micron order (Kim, D. Y., and Rhee, Y. H.: Biodegradation of microbial and synthetic polyesters by fungi. Appl. Microbiol. Biotechnol., 61, 300-308 (2003)). Uchida et al. have isolated *Acidovolax delafieldii* strain BS-3 which assimilates PBSA pellets as a sole carbon source JP 11-225755 A entitled "Biodegradable polymer-degrading enzyme and method for its preparation" (Applicant: Mitsubishi Chemical Corporation; Inventors: Toshiaki Nakajima, et al.); and Uchida, H., Nakajima-Kambe, T., Shigeno-Akutsu, Y., Nomura, N., Tokiwa, Y., and Nakahara, T.: Properties of a bacterium which degrades solid poly(tetramethylene succinate)-co-adipate, a biodegradable plastic. FEMS Microbiology Letters, 189, 25-29, (2000)], but there is no other report about bacteria capable of degrading solid pellets.

As for polylactic acid, there is a report of a degrading enzyme derived from actinomycetes *Amycolatopsis* sp. strain K104-1, but degradation in film form requires 48 hours or more and degradation of PBSA is not discussed in this report (Nakamura K, Tomita T, Abe N, and Kamio Y.: Purification and characterization of an extracellular poly(L-lactic acid) depolymerase from a soil isolate, *Amycolatopsis* sp. strain K104-1. Appl. Environ. Microbiol. 67, 345-353 (2001)). Likewise, a polylactic acid-degrading enzyme derived from *Peanibacillus amylolyticus* strain TB-13 [Akutsu-Shigeno, Y., Teeraphatpornchai, T., Teamtisong, T., Nomura, N., Uchiyama, H., Nakahara, T., and Nakajima-Kambe, T.: Cloning and sequencing of a poly(DL-lactic acid) depolymerase gene from *Peanibacillus amylolyticus* strain TB-13 and its functional expression in *Escherichia coli*. Appl. Environ. Microbiol., 69, 2498-2504 (2003); and JP 2004-166540 A entitled "Novel plastic-degrading enzymes and genes encoding the enzymes" (Applicant: Japan Science and Technology Agency, Inventors: Toshiaki Nakajima, et al.)] also allows degradation of polybutylenesuccinate-co-adipate (PBSA), but the degradation is less successful and limited to the emulsion form.

On the other hand, as for polybutylenesuccinate-co-adipate (PBSA), there are many reports of degrading bacteria, and enzymes derived from mold strains have been partially purified. However, no attempt has been made to purify bacterial enzymes. A PBSA-degrading enzyme and cloning of its gene are reported for *Acidovolax delafieldii* strain BS-3 [JP 11-225755 A entitled "Biodegradable polymer-degrading enzyme and method for its preparation" (Applicant: Mitsubishi Chemical Corporation; Inventors: Toshiaki Nakajima, et al.); and Uchida, H., Y. Shigeno-Akutsu, N. Nomura, T. Nakahara, and Nakajima-Kambe, T.: Cloning and Sequence Analysis of Poly(tetramethylene succinate) Depolymerase from *Acidovorax delafieldii* Strain BS-3. J. Biosci. Bioeng., 93, 245-247 (2002)], but this enzyme has low degrading ability and allows only degradation in emulsion form, but not in film form.

In view of the foregoing, there are a limited number of reports on microorganisms capable of degrading plastics in film or pellet form, and further their enzymes are poorly known. To establish enzymatic recycling, there is a strong demand for enzymes capable of rapidly degrading solid plastics.

In addition to recycling, as proper treatment for biodegradable plastics, degrading bacteria have a potential for being added to a kitchen refuse treater and/or for composting. In this case, such bacteria are desired to successfully degrade plastics even in a nutritious environment. However, many previous degrading microorganisms use the plastics as a sole carbon source, and hence their degrading ability is significantly decreased or lost in the presence of other organic materials at high concentrations. There have been few cases to search for microorganisms allowing degradation in a nutritious environment.

DISCLOSURE OF THE INVENTION

Problems to be Solved by the Invention

An object of the present invention is to provide a novel microorganism capable of degrading plastics, and a method for degrading plastics or for collecting monomers using the microorganism. In particular, the present invention aims to provide a microorganism capable of degrading solid plastics with high activity even in a nutritious environment. Another object of the present invention is to provide a novel polyester-based-plastic-degrading enzyme capable of degrading solid plastics and a polynucleotide encoding the enzyme, as well as a method for degrading plastics or for collecting monomers using the enzyme or a microorganism expressing the enzyme.

Means for Solving the Problems

To achieve the objects stated above, a search was made to obtain, from the natural world, novel bacteria which degrade polyester-based solid plastics in the presence of organic materials.

The inventors of the present invention have screened microorganisms which degrade plastics, particularly those having ester bonds in the molecular structure, by using polybutylenesuccinate-co-adipate (PBSA) as a sample, and have found that microorganisms belonging to the genus *Leptothrix* have the ability to degrade the above plastic in solid form (It should be noted that microorganisms belonging to the genus *Leptothrix* were not previously known to have any ability to degrade the above plastic). The inventors have also found a method for degrading plastics or for collecting monomers using such a microorganism belonging to the genus *Leptothrix*.

Namely, the present invention provides a microorganism belonging to the genus *Leptothrix* and having the ability to degrade plastics, particularly solid plastics having ester bonds in the molecular structure, as well as providing a method for degrading plastics or for collecting monomers using the microorganism belonging to the genus *Leptothrix*.

The present invention is directed to an enzyme having the ability to degrade plastics, particularly solid plastics having ester bonds in the molecular structure, which is produced by *Leptothrix* sp. strain TB-71 (Accession No. FERM BP-10204) deposited on Jan. 20, 2005, with the International Patent Organism Depositary, the National Institute of Advanced Industrial Science and Technology, AIST Tsukuba Central 6, 1-1, Higashi 1-chome Tsukaba-shi, Ibaraki-ken 305-8566 in Japan under terms of the Budapest Treaty. The present invention is also directed to a polynucleotide encoding the enzyme, and a method in which a host carrying the polynucleotide is allowed to express an enzyme having the ability to degrade plastics, followed by purification to obtain the enzyme.

The present invention is further directed to a method for degrading plastics or for collecting monomers using the enzyme or a host expressing the enzyme.

The enzyme of the present invention has the ability to degrade plastics, particularly solid plastics having ester bonds in the molecular structure. More specifically, the enzyme of the present invention is a novel plastic-degrading enzyme derived from, e.g., *Leptothrix* spp.

BRIEF DESCRIPTION OF DRAWINGS

FIG. 1 shows an evolution dendrogram of the strain TB-71 and its related strains.

FIG. 2 shows the time course of PBSA disk degradation by the strain TB-71.

FIG. 3 shows a flow chart for preparing a crude enzyme solution.

FIG. 4 shows the results examined for the optimum pH of a PBSA-degrading enzyme derived from the strain TB-71.

FIG. 5 shows the results examined for the optimum temperature of a PBSA-degrading enzyme derived from the strain TB-71.

FIG. 6 shows the results examined for the temperature stability (for 30 minutes) of a PBSA-degrading enzyme derived from the strain TB-71.

FIG. 7 shows procedures for extracting the chromosomal total DNA of the strain TB-71.

FIG. 8 shows the restriction map of pBSL1.

FIG. 9 shows the PBS-degrading activity of subcloned fragments, along with the putative ORF region.

FIG. 10 shows the entire amino acid sequence of a PBSA-degrading enzyme gene product (PbsLA) (SEQ ID NO: 4). The signal sequence is shown in bold type.

FIG. 11 shows the entire nucleotide sequence of a PBSA-degrading enzyme gene (pbsLA) (SEQ ID NO: 5).

BEST MODE FOR CARRYING OUT THE INVENTION

Microorganism

Microorganisms belonging to the genus *Leptothrix* and having the ability to degrade solid plastics may be either known or newly screened microorganisms.

By way of example, screening of microorganisms may be accomplished as follows. Soil samples collected from various areas are diluted appropriately with physiological saline and applied onto NB agar plates overlaid with emulsified PBSA, followed by culturing at 30° C. to obtain strains which form clear zones around colonies. If necessary, as a secondary screening step, PBSA pellets are added to test tubes containing NB liquid medium and the candidate strains obtained from the above screening are inoculated into the tubes. Samples showing a difference in the weight of PBSA before and after culturing are defined as candidate strains.

The microorganism of the present invention is not limited in any way as long as it belongs to the genus *Leptothrix* and has the ability to degrade plastics, particularly solid plastics having ester bonds in the molecular structure. More specifically, typical examples include *Leptothrix* sp. strain TB-71 (Accession No. FERM BP-10204) deposited on Jan. 20, 2005, with the International Patent Organism Depositary, the National Institute of Advanced Industrial Science and Technology in Japan (Central 6, 1-1-1 Higashi, Tsukuba, Japan) under terms of the Budapest Treaty. Mycological properties of *Leptothrix* strains can be found in, for example, BERGEY'S MANUAL OF Systematic Bacteriology (vol. 1, 1984, vol. 2, 1986, vol. 3, 1989, vol. 4, 1989).

Moreover, the microorganism of the present invention may be either a wild-type or mutant strain as long as it is a *Leptothrix* strain having the ability to degrade plastics, particularly solid plastics having ester bonds in the molecular structure.

Mutant strains may be obtained by mutagenesis with ethylmethanesulfonic acid (a conventionally commonly used mutagen), treatment with other chemical substances (e.g., nitrosoguanidine, methylmethanesulfonic acid), ultraviolet irradiation, or so-called spontaneous mutation without using any mutagen.

Any medium can be used without particular limitation in culturing microorganisms belonging to the genus *Leptothrix* as long as it allows growth of microorganisms belonging to the genus *Leptothrix*. Examples include, but are not limited to, LB medium (1% tryptone, 0.5% yeast extract, 1% NaCl) and NB medium. More specifically, the medium used for, growing the microorganism of the present invention may contain a carbon source (e.g., glucose) assimilable by the microorganism of the present invention and a nitrogen source assimilable by the microorganism of the present invention. Such a nitrogen source includes an organic nitrogen source such as peptone, meat extract, yeast extract or corn steep liquor, as well as an inorganic nitrogen source such as ammonium sulfate or ammonium chloride. If desired, the medium may further contain salts composed of cations (e.g., sodium ion, potassium ion, calcium ion, magnesium ion) and anions (e.g., sulfate ion, chlorine ion, phosphate ion). Moreover, the medium may also be supplemented with trace components such as vitamins and nucleic acids. The concentration of a carbon source ranges from, e.g., around 0.1% to 10%, while the concentration of a nitrogen source will vary depending on its type, but ranges from, e.g., around 0.01% to 5%. The concentration of an inorganic salt ranges from, e.g., around 0.001% to 1%.

Solid plastics which can be degraded in the present invention have ester bonds in the molecular structure of the plastics, and preferably include polybutylenesuccinate-co-adipate, polyethylenesuccinate or polycaprolactone. It should be noted that this enzyme is capable of degrading not only solid plastics, but also plastics even in liquid or gel form. As used herein, the term "solid" or the phrase "in solid form" means a solid form such as films and pellets.

Polybutylenesuccinate-co-adipate refers to a polymer prepared by adding adipic acid to source materials during polybutylenesuccinate synthesis. The melting point decreases to around 90° C., but the flexibility is improved. This polymer is used in packaging materials, seedling pots, garbage bags, etc. There is no particular limitation on the number average molecular weight of polybutylenesuccinate-co-adipate which can be treated by the degradation method of the present invention.

Polyethylenesuccinate refers to a polymer obtained by replacement of butanediol in polybutylenesuccinate with ethylene glycol. This polymer is expected for use in food films because of its low permeability to oxygen although it has mechanical properties comparable to those of polyethylene or polypropylene and a lower melting point of 100° C. There is no particular limitation on the number average molecular weight of polyethylenesuccinate which can be treated by the degradation method of the present invention.

Polycaprolactone refers to a thermoplastic polyester which is synthesized by ring-opening polymerization of ε-caprolactone and is flexible even at a considerably low temperature. There is no particular limitation on the number average molecular weight of polycaprolactone which can be treated by the degradation method of the present invention.

Further, the present invention provides a method for degrading plastics, particularly solid plastics having ester bonds in the molecular structure by the action of microorganisms. This method is based on a phenomenon that plastics are degraded and consumed as a nutrient source during growth of microorganisms, or on the action of microbial enzymes to degrade plastics, i.e., on the use of grown microorganism cells such as resting cells.

Monomers from plastics can be collected after the above degradation process by collecting monomers generated as a result of the degradation.

Alternatively, before being provided for treatment of solid plastics, microorganism cells may be lyophilized in a routine manner to give a cell powder, and may further be blended with various vitamins, minerals and necessary nutrient sources (e.g., yeast extract, casamino acid, peptone) for formulation into solid preparations including tablets. Likewise, strains per se may also be used as components of activated sludge and compost.

Solid plastics to be degraded may be added in emulsion or powder form to a liquid medium or may be added in massive form such as films or pellets. It should be noted that the amount of plastics added to the medium is desirably 0.01% to 10% by weight. Microorganisms may be added in a very small amount; and it is preferable to use them in an amount of 0.1% by weight or more (wet weight) relative to plastics in consideration of degradation efficiency. Plastics to be degraded may be provided either alone or in combination.

In an embodiment based on a phenomenon in which plastics are degraded and consumed as a nutrient source during growth of microorganisms, plastics may be provided as a sole carbon source or together with other carbon sources. The microorganism of the present invention belonging to the genus *Leptothrix* is characterized by allowing degradation of solid plastics even in a nutritious environment. The medium available for use may contain a plastic(s) or glucose or the like as a carbon source, as well as a nitrogen source assimilable by the microorganism of the present invention, including an organic nitrogen source (e.g., peptone, meat extract, yeast extract, corn steep liquor) or an inorganic nitrogen source (e.g., ammonium sulfate, ammonium chloride). If desired, the medium may further contain inorganic salts composed of cations (e.g., sodium ion, potassium ion, calcium ion, magnesium ion) and anions (e.g., sulfate ion, chlorine ion, phosphate ion). Moreover, the medium may also be supplemented with trace components such as vitamins and nucleic acids. The concentration of a carbon source ranges from, e.g., around 0.1% to 10%, while the concentration of a nitrogen source will vary depending on its type, but ranges from, e.g., around 0.01% to 5%. The concentration of an inorganic salt ranges from, e.g., around 0.001% to 1%.

In an embodiment using the action of microbial enzymes to degrade plastics, i.e., in an embodiment using grown microorganism cells such as resting cells, since there is no need to grow the microorganisms during degradation of plastics, the medium may be a buffer containing a solid plastic(s), which may further be supplemented with nitrogen sources, inorganic salts, vitamins, etc. Examples of a buffer include phosphate buffer.

The time required for degradation of solid plastics will vary depending on the type, composition, shape and amount of plastics to be degraded, the type and amount (relative to resins) of microorganisms used, as well as various culture conditions, etc.

In the present invention, degradation of plastics can be observed when static culture, shaking culture or aeration culture is performed on the above microorganisms under aerobic conditions. Preferred is rotary shaking culture, a rotation speed of which may be in the range of 30 to 250 rotations per minute. In relation to culture conditions, the culture temperature may be 10° C. to 50° C., particularly preferably around 30° C. The pH of the medium may be in the range of 4 to 10, preferably around 7.

Degradation of plastics in the medium can be confirmed, e.g., by measuring the weight loss of plastics provided for degradation or by measuring clear zones formed as a result of degradation of plastics when provided as an emulsion.

Enzyme

The enzyme of the present invention is a polypeptide composed of 283 amino acids and having a molecular weight of 29812.58, which is defined by the amino acid sequence shown in amino acids 1-283 of SEQ ID NO: 4. This amino acid sequence is that of a polypeptide encoded by the open reading frame region of the nucleotide sequence shown in SEQ ID NO: 3.

It should be noted that the open reading frame of SEQ ID NO: 5 has a signal peptide region and its cleavage point is located between the 24th and 25th amino acids from the N-terminus of SEQ ID NO: 4.

The amino acid sequence of the present invention includes the amino acid sequence shown in SEQ ID NO: 4, as well as analogs and derivatives thereof. Moreover, corresponding homologous amino acid sequences derived from other microorganisms are also encompassed by the present invention. Further, any polypeptide encoded by the nucleotide sequence of SEQ ID NO: 5 also falls within the scope of the present invention.

Polypeptides derived from the polypeptide shown in SEQ ID NO: 4 by partial deletion, substitution, insertion or addition of amino acids, e.g., polypeptides comprising substitution of up to 20 amino acids, preferably up to 10 amino acids, and more preferably up to 5 amino acids in the amino acid sequence shown in SEQ ID NO: 4 may have the same enzyme activity. Thus, these peptides also fall within the enzyme of the present invention as long as they have the same enzyme activity. Moreover, such polypeptides share at least 70% homology, preferably at least 80% homology, and more preferably at least 90% homology with the amino acid sequence shown in SEQ ID NO: 4 (Homology calculation can be accomplished, e.g., by using the BLAST (Basic Local Alignment Search Tool) search). Such polypeptides also fall with the scope of the present invention as long as they are characterized by catalyzing solid plastic degradation.

Solid plastics which can be degraded by this enzyme have ester bonds in the molecular structure of the plastics. Non-limiting examples include polybutylenesuccinate-co-adipate, polyethylenesuccinate and polycaprolactone. It should be noted that this enzyme is capable of degrading not only solid plastics, but also plastics even in liquid or gel form. As used herein, the term "solid" or the phrase "in solid form" means a solid form such as films and pellets.

Polybutylenesuccinate-co-adipate refers to a polymer prepared by adding adipic acid to source materials during polybutylenesuccinate synthesis. The melting point decreases to around 90° C., but the flexibility is improved. This polymer is used in packaging materials, seedling pots, garbage bags, etc. There is no particular limitation on the number average molecular weight of polybutylenesuccinate-co-adipate which is degraded by the enzyme of the present invention.

Polyethylenesuccinate refers to a polymer obtained by replacement of butanediol in polybutylenesuccinate with ethylene glycol. This polymer is expected for use in food films because of its low permeability to oxygen although it has mechanical properties comparable to those of polyethylene or polypropylene and a lower melting point of 100° C. There is no particular limitation on the number average molecular weight of polyethylenesuccinate which can be treated by the degradation method of the present invention.

Polycaprolactone refers to a thermoplastic polyester which is synthesized by ring-opening polymerization of $\epsilon$-caprolactone and is flexible even at a considerably low temperature. There is no particular limitation on the number average molecular weight of polycaprolactone which can be treated by the degradation method of the present invention.

Gene

Next, a gene encoding the enzyme of the present invention is a polynucleotide encoding a polypeptide consisting of an amino acid sequence encoded by the open reading frame of SEQ ID NO: 5. For example, it is a polynucleotide containing the nucleotide sequence represented by nucleotides 1-849 shown in SEQ ID NO: 5 of the Sequence Listing.

The polynucleotide of the present invention may include degenerate variants thereof. The term "degenerate" or "degeneracy" means a phenomenon that different nucleotide codons may encode the same amino acid. Thus, the nucleotide sequence of a nucleic acid molecule encoding the plastic-degrading enzyme of the present invention may vary due to the degeneracy.

In the present invention, proteins encoded by the nucleotide sequence shown in SEQ ID NO: 5 and a nucleotide sequence hybridizing to a sequence complementary to the nucleotide sequence shown in SEQ ID NO: 5 under highly stringent conditions [e.g., hybridization to filter-bound DNA in 0.5 M $NaHPO_4$, 7% sodium dodecyl sulfate (SDS), 1 mM EDTA at 65° C. and washing in 0.1×SSC/0.1% SDS at 68° C. (Ausubel, F. M. et al. ed., 1989, Current Protocols in Molecular Biology, Vol. I, Green Publishing Associates, and John Wily & Sons, New York, p. 2.10.3)] may have the same enzyme activity. Thus, these nucleotide sequences also fall within the scope of the present invention as long as they have the same enzyme activity. Moreover, proteins encoded by nucleotide sequences hybridizing to a sequence complementary to the nucleotide sequence shown in SEQ ID NO: 5 under moderately stringent conditions [e.g., washing in 0.2×SSC/ 0.1% SDS at 42° C. (Ausubel, et al., 1989, supra)] may have the same enzyme activity. Thus, these nucleotide sequences also fall within the scope of the present invention as long as they have the same enzyme activity.

According to gene recombination technology, it is possible to induce an artificial mutation at a specific site of basic DNA without altering basic properties of the DNA or to improve the properties. The polynucleotide having the native nucleotide sequence provided by the present invention or a polynucleotide having a nucleotide sequence different from the native sequence can also be modified to have properties equal or superior to those of the native polynucleotide by artificial insertion, deletion, substitution or addition. Such a mutated polynucleotide also falls within the scope of the present invention. Namely, polynucleotides derived from the polynucleotide shown in SEQ ID NO: 5 of the Sequence Listing by partial insertion, deletion, substitution or addition refer to polynucleotides comprising substitution of up to 20 nucleotides, preferably up to 10 nucleotides, and more preferably up to 5 nucleotides in the nucleotide sequence shown in SEQ ID NO: 5. Moreover, such polynucleotides share at least 70% homology, preferably at least 80% homology, and more preferably at least 90% homology with the nucleotide sequence shown in SEQ ID NO: 5 (Homology calculation can be accomplished, e.g., by using the BLAST (Basic Local Alignment Search Tool) search). Such polynucleotides also fall within the scope of the present invention as long as they encode polypeptides characterized by having the ability to degrade solid plastics.

Method for Enzyme Production

The enzyme of the present invention can be produced by culturing a microorganism belonging to the genus *Leptothrix* and having the ability to degrade solid plastics, and then separating and purifying the enzyme in the microorganism, or by culturing a host carrying the polynucleotide sequence of the present invention, and then separating and purifying the enzyme from the host.

Microorganisms belonging to the genus *Leptothrix* and having the ability to degrade plastics may be either known or newly screened microorganisms. More specifically, typical examples include *Leptothrix* sp. strain TB-71 (Accession No. FERM BP-10204) deposited on Jan. 20, 2005 with the International Patent Organism Depositary, the National Institute of Advanced Industrial Science and Technology in Japan. By way of example, screening of microorganisms may be accomplished as follows. Soil samples collected from various areas are diluted appropriately with physiological saline and applied onto NB agar plates overlaid with emulsified PBSA, followed by culturing at 30° C. to obtain strains which form clear zones around colonies. If necessary, as a secondary screening step, PBSA pellets are added to test tubes containing NB liquid medium and the candidate strains obtained from the above screening are inoculated into the tubes. Strains obtained from samples showing a difference in the weight of PBSA before and after culturing are defined as candidate strains.

Any medium can be used without particular limitation in culturing microorganisms belonging to the genus *Leptothrix* as long as it allows growth of microorganisms belonging to the genus *Leptothrix*. Examples include, but are not limited to, LB medium (1% tryptone, 0.5% yeast extract, 1% NaCl) and NB medium. More specifically, the medium used for growing the microorganism of the present invention may contain a carbon source (e.g., glucose) assimilable by the microorganism of the present invention and a nitrogen source assimilable by the microorganism of the present invention. Such a nitrogen source includes an organic nitrogen source such as peptone, meat extract, yeast extract or corn steep liquor, as well as an inorganic nitrogen source such as ammonium sulfate or ammonium chloride. If desired, the medium may further contain salts composed of cations (e.g., sodium ion, potassium ion, calcium ion, magnesium ion) and anions (e.g., sulfate ion, chlorine ion, phosphate ion). Moreover, the medium may also be supplemented with trace components such as vitamins and nucleic acids. The concentration of a carbon source ranges from, e.g., around 0.1% to 10%, while the concentration of a nitrogen source will vary depending on its type, but ranges from, e.g., around 0.01% to 5%. The concentration of an inorganic salt ranges from, e.g., around 0.001% to 1%.

A method for producing the enzyme of the present invention by recombinant cells is as follows. First, a polynucleotide molecule is inserted into any vector which can be introduced into host cells to form a recombinant. The vector may be either RNA or DNA, either prokaryotic or eukaryotic, and typically is a virus or a plasmid. The vector may be expressed as an extrachromosomal element (e.g., as a plasmid) or may be integrated into the chromosome. The integrated polynucleotide molecule may be under the control of a chromosomal promoter, under the control of its native promoter or a plasmid promoter, or under the control of a multiple promoter combination. Single or multiple copies of the polynucleotide molecule may be integrated into the chromosome. The vector is then transfected into host cells to form recombinant cells. Host cells suitable for transfection include any transfectable cells such as bacteria, fungi (e.g., yeast), insect, plant or animal cells. Host cells preferred for use in the present invention include, but are not limited to, any microorganism cells suitable for expressing the enzyme of the present invention, such as *E. coli, Leptothrix* spp., *Bacillus subtilis* and yeast cells. The host is further cultured under culture conditions suitable for the host to thereby obtain recombinant cells containing the enzyme of the present invention. Culture conditions suitable for the host are well known to those skilled in the art.

Separation and purification of the enzyme of the present invention from microorganisms belonging to the genus *Leptothrix* and having the ability to degrade solid plastics or from host cells carrying the polynucleotide sequence of the present invention may be accomplished by using techniques commonly used for protein separation/purification from cells.

More specifically, any commonly used separation/purification means may be used for this purpose after cell homogenization. Non-limiting examples for cell homogenization include ultrasonication, high-pressure homogenizer treatment, and osmotic shock. Examples of separation/purification means include salting-out, gel filtration, and ion exchange chromatography, which may be used in combination as appropriate. Further, in the case of enzyme production by gene recombination technology, a recombinant enzyme is produced to have a His-tag at its C-terminus, the cultured cells are collected by centrifugation, and the periplasmic fraction is extracted by osmotic shock, whereby the recombinant enzyme can be readily purified with a nickel-chelating column because it has a His-tag at its C-terminus.

Method for Degrading Plastics and Method for Collecting Monomers

The present invention further provides a method for degrading plastics, particularly solid plastics having ester bonds in the molecular structure, as well as a method for collecting monomers, wherein each method uses the enzyme of the present invention or a microorganism expressing the enzyme. Namely, the method of the present invention for degrading plastics is based on the action of the enzyme to degrade plastics, on a phenomenon in which plastics are degraded and consumed as a nutrient source during growth of a microorganism expressing the enzyme, or on the use of microorganism cells expressing the enzyme (e.g., resting cells).

Monomers from plastics can be collected after the above degradation process by collecting monomers generated as a result of the degradation.

Alternatively, before being provided for treatment of plastics, microorganism cells expressing the enzyme of the present invention may be lyophilized in a routine manner to give a cell powder, and may further be blended with various vitamins, minerals and necessary nutrient sources (e.g., yeast extract, casamino acid, peptone) for formulation into solid preparations including tablets. Likewise, microorganism strains expressing the enzyme per se may also be used as components of activated sludge and compost.

The enzyme of the present invention may be provided for use in tablet or other forms containing the enzyme. In addition to a crude solution, crude powder or purified form of the enzyme, other components commonly used for enzyme tablets or the like, such as a stabilizer, an excipient, a pH adjustor, an extender and a binder, may be blended as appropriate. The dosage form is also not limited in any way and may be selected from powders, granules, tablets and other dosage forms, depending on the intended purpose.

The enzyme used in the method of the present invention is not limited to an enzyme produced by *Leptothrix* sp. strain TB-71 (Accession No. FERM BP-10204), and it is also possible to use an enzyme produced by a microorganism generated by recombinant DNA technology, such as a host (e.g., *E. coli, Leptothrix* spp., *Bacillus subtilis*, yeast) carrying a polynucleotide encoding the enzyme ligated to an expression vector.

The generation of microorganisms by recombinant DNA technology may be accomplished by using techniques commonly used in the art. For example, a high-efficiency expression system for plastic-degrading enzyme genes can be constructed by using a pET system which is one of the most currently efficient host-vector systems for polypeptide expression.

The enzyme used in the method of the present invention is not necessarily required to be fully purified, but when enzyme purification is desired, techniques commonly used for protein purification, such as salting-out, gel filtration and ion exchange chromatography, may be used in combination as appropriate. By way of example, a recombinant enzyme is produced to have a His-tag at its C-terminus, the cultured cells are collected by centrifugation, and the periplasmic fraction is extracted by osmotic shock. The recombinant enzyme can be readily purified with a nickel-chelating column because it has a His-tag at its C-terminus.

Plastics which can be degraded by the method of the present invention for degrading plastics have ester bonds in the molecular structure of the plastics, as described above. Non-limiting examples include polybutylenesuccinate-co-adipate, polyethylenesuccinate, and polycaprolactone.

Plastics to be degraded may be added in emulsion or powder form to a liquid medium or may be added in massive form such as films or pellets. It should be noted that the amount of plastics added to the medium is desirably 0.01% to 10% by weight. The enzyme or microorganism may be added in a very small amount; and it is preferable to use the same in an amount of 0.001% by weight or more (wet weight) for the enzyme and 0.1% by weight or more (wet weight) for the microorganism, relative to plastics in consideration of degradation efficiency. Plastics to be degraded may be provided either alone or in combination.

In an embodiment using the action of purified or crude enzymes to degrade plastics, the medium for plastic degradation may be a buffer containing a plastic(s), which may further be supplemented with nitrogen sources, inorganic salts, vitamins, etc. Examples of a buffer include phosphate buffer.

In an embodiment based on a phenomenon in which plastics are degraded and consumed as a nutrient source during growth of recombinant microorganisms expressing the enzyme of the present invention, culturing can be performed under culture conditions suitable for a host to be used, and such conditions are well known to those skilled in the art. Plastics may be provided as a sole carbon source or together with other carbon sources. Although the medium available for use is not limited in any way as long as it is a medium suitable for a microorganism to be used, it may contain glucose or the like as a carbon source, as well as a nitrogen source assimilable by the microorganism, including an organic nitrogen source (e.g., peptone, meat extract, yeast extract, corn steep liquor) or an inorganic nitrogen source (e.g., ammonium sulfate, ammonium chloride). If desired, the medium may further contain inorganic salts composed of cations (e.g., sodium ion, potassium ion, calcium ion, magnesium ion) and anions (e.g., sulfate ion, chlorine ion, phosphate ion). Moreover, the medium may also be supplemented with trace components such as vitamins and nucleic acids. The concentration of a carbon source ranges from, e.g., around 0.1% to 10%, while the concentration of a nitrogen source will vary depending on its type, but ranges from, e.g., around 0.01% to 5%. The concentration of an inorganic salt ranges from, e.g., around 0.001% to 1%.

In an embodiment using the action of recombinant microbial enzymes to degrade plastics, i.e., in an embodiment using grown microorganism cells such as resting cells, since there is no need to grow the microorganisms during degradation of plastics, the medium may be a buffer containing a plastic(s), which may further be supplemented with nitrogen sources, inorganic salts, vitamins, etc. Examples of a buffer include phosphate buffer.

In the present invention, in a case where enzyme-expressing recombinant microorganisms at the growth phase are used for plastic degradation, degradation of plastics can be observed when static culture, shaking culture or aeration culture is performed under aerobic conditions. Preferred is rotary shaking culture, a rotation speed of which may be in the range of 30 to 250 rotations per minute. In relation to culture conditions, the culture temperature may be 10° C. to 50° C., particularly preferably around 30° C. The pH of the medium may be in the range of 4 to 10, preferably around 7.

The time required for degradation of plastics will vary depending on the type, composition, shape and amount of plastics to be degraded, the type and amount (relative to resins) of microorganisms used, as well as various culture conditions, etc.

Degradation of plastics in the medium can be confirmed, e.g., by measuring the weight loss of plastics provided for degradation or by measuring clear zones formed as a result of degradation of plastics when provided as an emulsion.

EXAMPLES

The present invention will now be further described in more detail by way of the following examples, which are not intended to limit the scope of the invention.

Example 1

Screening of Microorganisms

Test Polyester

PBSA was used as a test polyester-based solid plastic. The PBSA used was Bionolle 3020 (average molecular weight: 140,000) manufactured by Showa Highpolymer Co., Ltd., Japan.

Procedures for Agar Plate Preparation

PBSA (2 g) was dissolved in 40 ml dichloromethane. This solution was added to 250 ml distilled water containing 40 mg of Plysurf A210G (a surfactant, Daiichi Kogyo Seiyaku Co., Ltd. Japan) and emulsified by stirring with a blender. This emulsion was stirred while being heated at 80° C. in a draft chamber to remove the solvent, and the resulting product was used as emulsified PBSA. An agar medium containing this emulsified PBSA was overlaid onto Nutrient broth (NB) agar plates.

Screening

Soil and river samples and activated sludge from water-purification plants around the Kanto region of Japan were used as screening sources. These samples were diluted appropriately with physiological saline and applied onto the NB agar plates overlaid with emulsified PBSA, followed by culturing at 30° C. to obtain bacteria forming clear zones around colonies.

As a secondary screening step, large test tubes (of 22 mm diameter) were charged with 10 ml NB liquid medium and provided for a degradation test on PBSA pellets. The degradation test was accomplished by using cylindrical pellets of 2.5 mm diameter and 4 mm long, which had been sterilized by soaking in 70% ethanol and aseptically dried in a clean bench before use.

After completion of culturing, the PBSA pellets were collected, washed with distilled water, dried and then weighed. A difference in the weight of PBSA before and after culturing was defined as the degraded amount.

Bacteria were extracted from 350 samples collected from environments such as soil, rivers and activated sludge. These bacteria were applied onto assay plates to separate 40 strains degrading emulsified PBSA around colonies and forming clear zones. The degradation test on PBSA pellets was performed on these strains to thereby separate the strain TB-71 showing disappearance of the pellet after 1 week of culturing, which was used for the subsequent studies.

Example 2

Identification of Microorganism

The full-length 16SrDNA was amplified from a single colony of the strain TB-71 by direct colony PCR using primers specific to 16SrDNA (27F: 5'-AGAGTTTGATCCTG-GCTCAG-3' (SEQ ID NO: 1) and 1494R: 5'-TGACTGACT-GAGGYTACCTTGTTAC-3' (SEQ ID NO: 2)). PCR conditions are as shown in Table 1. The PCR product was ligated to pGEM-T vector and used to transform an *E. coli* host strain, XL10gold. After overnight culturing on an ampicillin-containing agar plate, the plasmid was extracted from the resulting colonies, and the nucleotide sequence of the insert DNA was determined. A homology search was performed on the resulting nucleotide sequence using the BLAST program to prepare a dendrogram with the Clastal X software.

[Table 1]

TABLE 1

| PCR conditions | | |
|---|---|---|
| Reaction cycle | | |
| 94° C. | 2 minutes | |
| 98° C. | 15 seconds | |
| 60° C. | 20 seconds | } 30 cycles |
| 74° C. | 1 minute | |

As a result of the sequencing reaction, about a 640 bp nucleotide sequence was determined on the 5' side of the strain TB-71 16SrDNA. This sequence was subjected to DNA homology search (BLAST), indicating that its highest homology was 95% with *Leptothrix mobilis*, except for uncultured bacteria. When a dendrogram was prepared (FIG. 1), this strain was found to belong to the same cluster as the genus *Leptothrix*, but there is a high possibility that this strain is new because its highest homology to known species remains on the order of 95%.

Example 3

Degradation of Solid PBSA by Strain TB-71

Bionolle 3020 (300 mg, average molecular weight: 140, 000) was shaped into a disk of 25 mm diameter and 0.5 mm thickness and added to a 300 ml Erlenmeyer flask containing 50 ml NB medium. The disk had been soaked in 70% ethanol for 12 hours and then dried in a clean bench before use.

The strain TB-71 was cultured on a NB agar plate at 30° C. for 24 hours, suspended in physiological saline, and then inoculated at an initial cell concentration of $OD_{580}$=0.05. After a given period of time, the PBSA disk was collected, washed with distilled water, dried and then weighed. A difference in the weight of PBSA before and after culturing was defined as the degraded amount. To measure esterase activity, p-nitrophenyl acetate was used as a substrate and p-nitrophenol generated upon cleavage of the ester bond was measured by an increase in absorbance at 405 nm. The amount of the enzyme required to generate 1 μmol p-nitrophenol for 1 minute was defined as 1 unit.

The results obtained are shown in FIG. 2. The growth of this strain reached the maximum after 24 hours, but PBSA disk degradation slightly lagged behind the growth and the disk was completely degraded after 48 hours. In addition, esterase activity was observed in the culture solution over the course of degradation.

Example 4

Degradation of Various Polyester-Based Solid Plastics by Strain TB-71

As test polyester-based solid plastics, the following biodegradable plastics were further used in the degradation test: polybutylenesuccinate (PBS) (Bionolle 1020 and 1001 having a molecular weight of 140,000 and 260,000, respectively, manufactured by Showa Highpolymer Co., Ltd., Japan); polylactic acid (PLA) (Lacty having a molecular weight of 130,000, manufactured by Toyota Motor Corporation, Japan); and polyethylenesuccinate (PES) (Lunare SE having a molecular weight of 60,000, manufactured by Nippon Shokubai Co., Ltd., Japan). Likewise, additional PBSA with a different molecular weight (Bionolle 3001 having a molecular weight of 260,000, manufactured by Showa Highpolymer Co., Ltd., Japan) was also used. The same experimental procedure as shown above was repeated, i.e., 300 mg disks were prepared to measure the degraded amount, the bacterial growth amount and esterase activity after 72 hour culturing.

The results obtained are shown in Table 2. The strain had the activity to completely degrade a disk of higher molecular weight PBSA, Bionolle 3001. The strain also had a strong degrading activity for polyethylenesuccinate (Lunare SE). However, there was no degrading activity for polylactic acid. Interestingly, the strain was found to have no degrading activity for PBS, which is structurally very similar to PBSA. The reason for this result is not clear at present. Thus, this strain has clear substrate specificity in its activity to degrade polyester-based solid plastics and is suitable for selective monomerization.

[Table 2]

TABLE 2

Degradation of various polyester-based plastics by strain TB-71

| | Degraded amount (mg) | Growth (OD580) | Esterase activity (u/ml) |
|---|---|---|---|
| PBSA (Bionolle 3020) | 300 | 0.64 | 0.135 |
| PBSA (Bionolle 3001) | 300 | 0.54 | 0.135 |
| PBS (Bionolle 1020) | 3 | 0.57 | 0.059 |
| PBS (Bionolle 1001) | 4 | 0.67 | 0.038 |
| PLA (Lacty) | 0 | 0.59 | 0.047 |
| PES (Lunare SE) | 300 | 0.67 | 0.106 |

This strain completely degraded PBSA disks (about 300 mg) for 2 days. Previously known PBSA-degrading bacteria are almost exclusively emulsion- or film-degrading bacteria, and there are few reports on the degradation of solid matters such as pellets and disks. Plastic wastes are rarely provided in emulsion or film form, and hence it is absolutely necessary to provide the ability to degrade plastics in pellet or chip form when plastic wastes are to be adapted for monomer recycling. As an example of PBSA pellet-degrading bacteria, the previously reported *Acidovolax delafieldii* strain BS-3 can be presented (see Patent Document 2 and Non-patent Document 3). However, the strain TB-71 was shown to have the degrading ability at least 6 times stronger than that of the strain BS-3 which degrades about 150 mg of a PBSA disk for 7 days. Moreover, the BS-3 strain degrades PBSA as a sole carbon source, but has not yet been studied for its degrading ability in the presence of other organic nutrient sources. Further, there is no report of degrading bacteria of the genus *Leptothrix* including emulsion- or film-degrading bacteria.

Example 5

Purification of PBSA-Degrading Enzyme

Since preliminary studies had indicated that the PBSA-degrading enzyme of this strain was adhered to the cell surface, but not released into the culture solution, a further attempt was made to extract cell surface proteins with a surfactant during enzyme purification.

Example 5-1

Extraction of Crude Enzyme Solution from Bacterial Cells

The strain TB-71 was cultured on a NB plate at 30° C. for 2 days. A 300 ml Erlenmeyer flask was charged with 50 ml NB medium and inoculated with a loopful of the strain TB-71. To this flask, a PBSA disk (300 mg) of 25 mm diameter and 0.5 mm thickness was added and the cells were pre-cultured by shaking culture at 30° C., at 200 rpm for one day. Then, 500 ml NB medium (in a 3 liter Erlenmeyer flask) was inoculated with 50 ml of the pre-cultured solution and a PBSA disk (3 g) was added thereto, followed by shaking culture at 30° C., at 200 rpm for 2 days.

After completion of the main culture, the cultured solution was centrifuged at 8,000 rpm for 5 minutes to obtain the cells. The cells were washed with 0.1 M phosphate buffer, centrifuged again, and then suspended in 0.1 M phosphate buffer (10 ml). To this suspension, an equal volume of a 0.4% deoxy-BIGCHAP (nonionic surfactant) solution was added and stirred vigorously on ice for 30 minutes to extract proteins adhered to the cell surface. The suspension was then centrifuged at 15,000 rpm for 10 minutes to obtain the supernatant. After an equal volume of 0.1 M phosphate buffer was added to the supernatant, ammonium sulfate was added thereto at 40% saturation and stirred on ice for 30 minutes. After centrifugation to remove precipitates, ammonium sulfate was added at 60% saturation and stirred in the same manner, followed by centrifugation. The resulting precipitates were dissolved in 0.1 M phosphate buffer (2 ml) and provided as a crude enzyme solution. The flow chart is shown in FIG. 3.

Example 5-2

Enzyme Purification

A FPLC system (Pharmacia) was used to purify the crude enzyme solution. The crude enzyme solution was desalted using a desalting column (HiTrap Desalting, Pharmacia) and then applied to an anion exchange column (RESOURCE Q, Pharmacia; column volume: 1 ml) to collect the fraction passing through the column. The mobile phase used was 20 mM phosphate buffer (pH 7.0) at a flow rate of 2 ml/min. To this fraction, ammonium sulfate was added at 80% saturation and stirred on ice for 30 minutes, followed by centrifugation at 22,000 rpm for 30 minutes. The resulting precipitates were dissolved in 0.1 M phosphate buffer (2 ml) and applied to a gel filtration column (Superose12 HR16/50, Pharmacia). The mobile phase used was 20 mM phosphate buffer (pH 7.0) at a flow rate of 0.6 ml/min. Fractions having esterase activity were collected and supplemented with ammonium sulfate at 80% saturating concentration, followed by centrifugation.

The resulting precipitates were dissolved in 0.1 M phosphate buffer (1 ml) to obtain a purified enzyme sample.

Example 5-3

Measurement of Enzyme Activity

To measure PBSA-degrading activity, paper disks of 10 mm diameter were placed on PBSA emulsion agar plates and each solution (50 µl) was added dropwise to monitor emulsion degradation. Independently of this, to measure esterase activity, p-nitrophenyl acetate was used as a substrate and p-nitrophenol generated upon cleavage of the ester bond was measured by an increase in absorbance at 405 nm. The amount of the enzyme required to generate 1 µmol p-nitrophenol for 1 minute was defined as 1 unit.

A table of purification steps is shown below. The specific activity of this enzyme was increased about 4-fold by purification, and the yield was 56.2%. The purified sample showed a single band upon SDS-polyacrylamide gel electrophoresis. A molecular weight assay was made in SDS-polyacrylamide gel electrophoresis and gel filtration using molecular weight markers, suggesting that this enzyme was a monomeric form with a molecular weight of about 28,000.

[Table 3]

TABLE 3

Table of purification steps for PBSA-degrading enzyme

|  | Volume (ml) | Total protein (mg) | Total activity (U) | Specific activity (U/mg) | Purification (fold) | Yield (%) |
|---|---|---|---|---|---|---|
| Crude enzyme solution | 4.30 | 74.8 | 80.8 | 1.08 | 1.00 | 100 |
| Desalting column | 14.0 | 42.6 | 44.2 | 1.04 | 0.962 | 54.7 |
| RESOURCE Q | 2.00 | 16.8 | 55.0 | 3.27 | 3.03 | 68.1 |
| Superose12 | 1.12 | 10.8 | 45.4 | 4.20 | 3.89 | 56.2 |

Example 6

Various Properties of PBSA-Degrading Enzyme

Example 6-1

Examination of Optimum Reaction Conditions

To examine the optimum pH conditions, 0.1 M citrate buffer (pH 4.0-6.0), 0.1 M phosphate buffer (pH 6.0-8.0) and 0.1 M Tris-HCl buffer (pH 8.0-10.0) were used. The reaction was carried out at 30° C. to measure esterase activity at various pH values, provided that the measurement wavelength was set to 348 nm, instead of 405 nm, because the atomic absorption coefficient of p-nitrophenol would vary with pH and variations would be minimized at 348 nm. The optimum temperature was examined at pH 7. The temperature stability was examined at pH 7, and the enzyme was measured for its activity at 30° C. after being incubated at various temperatures for 30 minutes.

FIG. 4 shows, changes in activity at various pH values. This enzyme maintained high activity at the optimum pH widely ranging from around 5.5 to 9.0. Likewise, FIG. 5 shows the results examined for the optimum reaction temperature of this enzyme. This enzyme had high activity in the wide range between 25° C. and 55° C.

Moreover, FIG. 6 shows the results examined for the temperature at which this enzyme is stable. This enzyme was found to be stable against heating at 45° C. for 30 minutes, but deactivated at higher temperatures. It should be noted that this enzyme showed little decrease in its activity for several days at the minimum as long as it was kept at 40° C. or below.

Example 6-2

Degrading Activity for Various Polyester-Based Biodegradable Plastics

The PBSA and PBS used were Bionolle 3020 and 1020, respectively. Likewise, the PES and PLA used were Lunare SE and Lacty, respectively. The polyhydroxybutyrate-co-valerate (PHBV) and polycaprolactone (PCL) used were products of reagent grade manufactured by Wako Pure Chemical Industries, Ltd., Japan. Each plastic (0.2 g) was dissolved in 5 ml dichloromethane and casted on a Petri dish to form a film. Each film (0.3 mg) was added to a 1.7 Unit/ml enzyme solution (1 ml) and incubated at 30° C. for 1 hour, followed by measuring the total carbon content (TOC) in the solution.

The degrading activity of this enzyme for various polyester-based biodegradable plastics is shown in the table below. This enzyme was found to degrade PBSA, PEC and PCL, with the highest degrading activity for PCL. In each case, degradation was almost completed within 10 minutes and high degrading activity was confirmed. On the other hand, there was no degrading activity for PBS, PHBV and PLA. This substrate specificity was consistent with the results obtained for cultured cells of the strain TB-71.

[Table 4]

TABLE 4

Degrading activity of PBSA-degrading enzyme for various plastics

|  | Film weight (mg) | TOC in film (g/l) | Complete degradation | TOC in buffer after degradation (g/l) |
|---|---|---|---|---|
| PBSA | 3.0 | 1.700 | + | 2.020 |
| PBS | 3.0 | 1.674 | − | 0.187 |
| PES | 2.7 | 1.350 | + | 1.645 |
| PLA | 4.4 | 2.200 | − | 0.128 |
| PHBV | 2.8 | 1.561 | − | 0.124 |
| PCL | 3.0 | 1.895 | + | 2.587 |
| Control |  |  |  | 0.191 |

Moreover, PBSA degradation products generated by this enzyme were examined. The buffer after degradation was subjected to HPLC to analyze the degradation products. The column used was a BIO-RAD HPX-87H and the mobile phase used was 0.01 N sulfuric acid at a flow rate of 0.5 ml/min. The detector used was a differential refractometer (YRD-880, Shimamura Keiki, Japan).

As a result of the analysis, succinic acid and 1,4-butanediol were detected and their concentrations were consistent with the theoretical values calculated for complete degradation and monomerization of PBSA. This indicates that this enzyme completely degrades PBSA into monomers.

Example 6-3

Determination of N-Terminal Amino Acid Sequence

The purified sample of the PBSA-degrading enzyme derived from the strain TB-71 was blotted onto a PVDF membrane, and the inventors asked the Toray Research Center (Japan) to analyze the N-terminal amino acid sequence.

An amino acid sequence covering from the N-terminus to the 10th residue of this enzyme was determined as follows (SEQ ID NO: 3).

Gly-Asn-Phe-Thr-Ala-Ser-Tyr-Ser-Ala-Gly (G)-(N)-
(F)-(T)-(A)-(S)-(Y)-(S)-(A)-(G)- [Formula 1]

*Amino acids in single-letter notation are shown in parentheses

Example 7

Cloning of Degrading Enzyme Gene by Shotgun Cloning (Extraction of DNA)
In accordance with the flow chart shown in FIG. 7, total DNA was extracted from the strain TB-71 cultured on a large scale in the same manner as used for enzyme purification.
(Shotgun Cloning)
The resulting chromosomal total DNA of the strain TB-71 was subjected to limited digestion with Sau3AI and then electrophoresed on an agarose gel to excise a DNA fragment fraction of approximately 2 to 5 kb, followed by DNA extraction using a GENECLEAN gel extraction kit (BIO101). The resulting fragment was ligated overnight at 14° C. to pUC118 which had been BamHI-digested and dephosphorylated, and then used to transform $E.$ $coli$ strain DH10B by electroporation. The $E.$ $coli$ cells were applied onto an ampicillin-containing LB agar medium overlaid with emulsified PBSA, followed by overnight culturing at 37° C. Since areas around colonies would become clear upon degradation of PBSA emulsion in the medium, clones having the degrading gene were selected using this phenomenon as an index.

A single strain forming a clear zone around its colony upon degradation of PBSA emulsion was obtained from about 35,000 transformant strains. A plasmid was extracted from this transformant and designated as pBSL1. pBSL1 was found to have a 2.4 kb gene fragment derived from the strain TB-71. Analyses using various restriction enzymes provided a restriction map as shown in FIG. 8.

pBSL1 was then digested with SacI, SphI or PstI. The resulting fragments were subcloned and used to transform $E.$ $coli$ DH10B. In the same manner as shown above, the $E.$ $coli$ cells were applied onto an assay medium overlaid with PBSA to determine the minimum region having PBSA-degrading activity. The PBS-degrading activity of each subcloned fragment was as shown in FIG. 9, thereby predicting the ORF region of the PBSA-degrading enzyme gene.

Example 8

Determination of Entire Nucleotide Sequence for PBSA-Degrading Enzyme Gene Derived from Strain TB-71 in pBSL1

Nucleotide sequencing was performed on pBSL-Sph shown in the above figure in a routine manner using a DNA sequencer.

As a result of a homology search, a single ORF was confirmed in the putative ORF region. This was designated as pbs LA. This gene was composed of 849 nucleotides and encoded a protein composed of 283 amino acids and having a molecular weight of 29812.58. Moreover, a sequence characteristic of the signal peptide was observed in N-terminal 24 amino acids of the ORF, and a sequence of 10 amino acids downstream of the signal cleavage position was completely consistent with the above sequence derived from the purified sample of the PBSA-degrading enzyme derived from the strain TB-71. The mature protein had a molecular weight of 27190.61, which was substantially consistent with the predicted molecular weight of the purified enzyme sample determined by SDS-polyacrylamide electrophoresis. This suggested that this ORF would be a gene encoding the PBSA-degrading enzyme of the strain TB-71. The isoelectric point was 8.42. The amino acid sequence and DNA sequence are shown in FIGS. 10 and 11, respectively.

Based on the resulting amino acid sequence, a BLAST homology search was performed against the DDBJ gene database of the National Institute of Genetics, Japan. The results indicated that this enzyme (gene) was a novel enzyme gene sharing no homology at amino acid level with any known gene.

Example 9

Integration of PBSA-Degrading Enzyme Gene into $E.$ $coli$ Expression Vector and Large Scale Expression of the Enzyme Primers were designed that were complementary to about 150 bp regions upstream and downstream of the PBSA-degrading enzyme gene (pbsLA) sequence including the signal sequence region. In this case, an NdeI site was added at the end of the forward primer, while an XhoI site was added at the end of the reverse primer. These primers were used for PCR to amplify pbsLA, which was then ligated to an $E.$ $coli$ expression vector, pET 21a(+), which had been digested with NdeI and XhoI. It should be noted that 6×His-Tag was added downstream of this ligated gene for the purpose of simplifying the subsequent purification. This vector was used to transform $E.$ $coli$ BL21(DE3), followed by overnight culturing at 30° C. The resulting transformant was cultured on a large scale and provided for enzyme purification.

The $E.$ $coli$ expression vector (pET 21a(+)) used in this experiment will increase expression levels in the presence of IPTG. However, in the case of this enzyme, IPTG addition reduced the enzyme activity. This would be because protein molecules highly expressed by IPTG addition associate to form an inclusion body and hence lose the activity. Moreover, this enzyme activity was accumulated within the cells, but not substantially secreted into the extracellular environment or the periplasm.

Next, after the cells were prepared on a large scale and homogenized by ultrasonication, an attempt was made to purify the gene product (recombinant PBSA-degrading enzyme). The cell homogenate was centrifuged to remove cell debris, followed by addition of ammonium sulfate at 30% saturation. After centrifugation to collect the supernatant, ammonium sulfate was further added thereto at 50% saturation. After centrifugation, the resulting precipitates were dissolved in 20 mM phosphate buffer and then purified using a Pharmacia Hi Trap Chelating column (Ni).

The purified recombinant enzyme was used to perform a degradation experiment on PBSA films. Test procedures were the same as shown above. The results indicated that this enzyme completely degraded PBSA films within 10 minutes and its activity was almost equal to that of the PBSA-degrading enzyme purified from the strain TB-71.

INDUSTRIAL APPLICABILITY

As described above, the microorganism of the present invention has the ability to degrade solid plastics and this degrading ability is very strong. Moreover, the microorganism of the present invention has the ability to degrade plastics even under nutritious conditions and also has clear substrate specificity, so that it is expected for use in enzymatic chemical recycling.

The enzyme of the present invention is suitable for use as an enzyme for monomer recycling because it maintains high activity over a wide pH range and is not substantially deactivated at 40° C. or below for several days. Also, the enzyme of the present invention is suitable for selective monomerization from a plastic mixture due to the enzyme's strict substrate specificity, which enables the enzyme to clearly distinguish its target plastics from the other plastics. Further, the gene encoding this enzyme is a completely novel gene sharing no significant homology with any of the previously known genes, and can be expected for use in further application areas such as organic synthesis once structural and functional analyses have been performed on the gene.

The invention claimed is:

1. An isolated solid plastic-degrading enzyme derived from a microorganism of the genus *Leptothrix* and comprising the amino acid sequence from glycine 25 to histidine 283 of SEQ ID NO: 4.

2. An isolated solid plastic-degrading enzyme comprising the amino acid sequence of SEQ ID NO: 4, wherein the isolated solid plastic-degrading enzyme optionally has a His-tag at a C-terminus of the amino acid sequence.

3. An isolated solid plastic-degrading enzyme, comprising the amino acid sequence of SEQ ID NO: 4 with a deletion of the N-terminal 24 amino acid residues of SEQ ID NO:4, wherein the isolated solid plastic-degrading enzyme optionally has a His-tag at a C-terminus of the amino acid sequence.

4. The isolated enzyme according to claim 1, wherein the isolated enzyme is capable of degrading a plastic having ester bonds in the molecular structure.

5. The isolated enzyme according to claim 1, wherein the isolated enzyme is capable of degrading polybutylenesuccinate-co-adipate, polyethylenesuccinate or polycaprolactone.

6. A method for producing the enzyme according to claim 1, which comprises the steps of:
    culturing a microorganism of the genus *Leptothrix*;
    selecting a *Leptothrix* microorganism capable of degrading plastic; and
    separating and purifying the plastic degrading enzyme according to claim 1 from the selected *Leptothrix* microorganism.

7. The isolated enzyme according to claim 1, which is in a purified form.

8. The isolated enzyme according to claim 1, which is in a purified form and is obtained from *Leptothrix* sp. strain TB-71 (Accession No. FERM BP-10204).

9. The method according to claim 6, wherein the microorganism is *Leptothrix* sp. strain TB-71 (Accession No. FERM BP-10204).

10. A method for degrading a plastic, which comprises the step of bringing the plastic into contact with an isolated microorganism belonging to the genus *Leptothrix* having the ability to degrade a plastic or a mutant strain thereof, wherein the microorganism expresses a solid plastic-degrading enzyme comprising the amino acid sequence from glycine 25 to histidine 283 of SEQ ID NO: 4.

11. The method according to claim 10, wherein the solid plastic-degrading enzyme consists of the amino acid sequence from glycine 25 to histidine 283 of SEQ ID NO: 4.

12. The isolated enzyme according to claim 1, wherein the isolated enzyme comprises the amino acid sequence of SEQ ID NO: 4.

13. The isolated enzyme according to claim 1, wherein the isolated enzyme consists of the amino acid sequence from glycine 25 to histidine 283 of SEQ ID NO: 4.

14. The method according to claim 10, wherein the solid plastic-degrading enzyme comprises the amino acid sequence of SEQ ID NO: 4.

15. The method according to claim 10, wherein the microorganism belonging to the genus *Leptothrix* is *Leptothrix* sp. strain TB-71 (Accession No. FERM BP-10204).

16. The method according to claim 10, wherein the plastic is in solid form and has ester bonds in the molecular structure.

17. The method according to claim 10, wherein the plastic is polybutylenesuccinate-co-adipate, polyethylenesuccinate or polycaprolactone.

18. A method for degrading a solid plastic, which comprises the step of bringing the solid plastic into contact with the enzyme according to claim 1.

19. The method according to claim 18, wherein the plastic has ester bonds in the molecular structure.

20. The method according to claim 18, wherein the plastic is polybutylenesuccinate-co-adipate, polyethylenesuccinate or polycaprolactone.

21. A method for degrading a solid plastic, which comprises the step of bringing the solid plastic into contact with a recombinant host expressing the enzyme according to claim 1.

22. The method according to claim 21, wherein the host is *E. coli*.

23. The method according to claim 21, wherein the plastic has ester bonds in the molecular structure.

24. The method according to claim 21, wherein the plastic is polybutylenesuccinate-co-adipate, polyethylenesuccinate or polycaprolactone.

* * * * *

UNITED STATES PATENT AND TRADEMARK OFFICE
CERTIFICATE OF CORRECTION

PATENT NO. : 7,960,154 B1  
APPLICATION NO. : 11/795578  
DATED : June 14, 2011  
INVENTOR(S) : Toshiaki Nakajima et al.

Page 1 of 1

It is certified that error appears in the above-identified patent and that said Letters Patent is hereby corrected as shown below:

ON THE TITLE PAGE:

At section (86), change:

"PCT No.: PCT/JP2006/000942"

to

--PCT No.: PCT/JP2006/300942--.

Signed and Sealed this  
Twenty-fifth Day of October, 2011

David J. Kappos  
*Director of the United States Patent and Trademark Office*

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Synthetic primer: 27F

<400> SEQUENCE: 1
agagtttgat cctggctcag                                                 20

<210> SEQ ID NO 2
<211> LENGTH: 25
<212> TYPE: DNA
<213> ORGANISM: Artificial Sequence
<220> FEATURE:
<223> OTHER INFORMATION: Synthetic primer: 1494R

<400> SEQUENCE: 2
tgactgactg aggytacctt gttac                                           25

<210> SEQ ID NO 3
<211> LENGTH: 10
<212> TYPE: PRT
<213> ORGANISM: Leptothrix sp.

<400> SEQUENCE: 3

Gly Asn Phe Thr Ala Ser Tyr Ser Ala Gly
1               5                   10

<210> SEQ ID NO 4
<211> LENGTH: 283
<212> TYPE: PRT
<213> ORGANISM: Leptothrix sp.

<400> SEQUENCE: 4

Met Gln Arg Arg Leu Ile Gln Arg Leu Ala Phe Leu Ala Ala Thr Thr
1               5                   10                  15

Val Phe Ala Gly Ser Ala Phe Ala Gly Asn Phe Thr Ala Ser Tyr Ser
            20                  25                  30

Ala Gly Leu Ser Ser Tyr Ser Ile Lys Gly Thr Glu Pro Asp Ser Gly
        35                  40                  45

Lys His Pro Val Phe Ile Tyr Thr Val Gly Thr Thr Glu Ser Tyr Asp
    50                  55                  60

Asn Ala Gln Ala Met Gly Ala Val Ala Glu Met Ala Ala Lys Gly Phe
65                  70                  75                  80

Val Ala Ala Ala Val Gln Tyr Asp Ser Ser Leu Phe Gly Thr Cys Ser
```

```
                    85                  90                  95
Gln Ile Leu Ser Lys Ala Arg Tyr Ile Tyr Asn Ser Gly Ser Thr Ser
                100                 105                 110

Ser Ala Ile Ser Lys Leu Cys Ser Arg Ala Ser Ala Asp Cys Ser Lys
            115                 120                 125

Gly Val Val Ala Gly Phe Ser Gln Gly Ser Val Ile Ala Leu Asn
        130                 135                 140

Ala Lys Asn Tyr Asp Ser Arg Val Arg Ala Ala Tyr Gly Met Gly Ser
145                 150                 155                 160

His Thr Ser Tyr Thr Thr Tyr Leu Met Ser Ser Cys Met Thr Pro Gly
                165                 170                 175

Gly Tyr Thr Ile Ser Lys Asp Asn Val Arg Ile Val Asn Gly Gln Ser
            180                 185                 190

Asp Ser Phe Pro Val Gly Thr Val Arg Ser Ser Glu Ser Val Ala
        195                 200                 205

Gly Arg Ser Cys Gly Ser Phe Ala Tyr Glu Cys Leu Ala Thr Asn Gly
    210                 215                 220

Ser Gly Trp Ile Met Ile Arg Asp Ser Asp Val Gly Asp Leu Ser Ala
225                 230                 235                 240

Asp His Cys Tyr Gln Arg Val Gly Gly Cys Thr Gly Leu Gln Ser Val
                245                 250                 255

Thr Asp Ser Thr Trp Arg Asn Gly Ser Thr Asn Trp Gly Leu Lys Ala
            260                 265                 270

Asn Leu Asn Trp Leu Asn Gly Phe Val Thr His
        275                 280

<210> SEQ ID NO 5
<211> LENGTH: 849
<212> TYPE: DNA
<213> ORGANISM: Leptothrix sp.

<400> SEQUENCE: 5
atgcaacgac gcctgatcca gcgcctggcc ttcctggccg ccaccaccgt cttcgccggc      60
agcgccttcg ccggcaactt cacgccagc tacagcgccg gcctgagcag ctacagcatc     120
aagggcaccg agcccgactc gggcaagcac ccggtgttca tctacaccgt gggcaccacc     180
gagagctacg acaacgccca ggccatgggc gccgtggccg agatggccgc caagggcttc     240
gtcgccgccg ccgtgcagta cgacagcagc ctgttcggca cctgctcgca gatcctgtcc     300
aaggcgcgct acatctacaa cagcggctcc accagcagcg ccatctcgaa gctgtgctcg     360
cgcgccagcg ccgactgctc caagggcgtg gtcgtcgccg gcttcagcca gggctcggtg     420
atcgccctca cgccaagaa ctacgacagc gcgtgcgtg ccgcctacgg catgggctcg      480
cacacgtcgt acacgaccta cctgatgagc tcgtgcatga cgccgggcgg ctacacgatc     540
tcgaaggaca cgtgcgcat cgtcaacggc cagagcgaca gcttcccggt cggcaccgtg     600
cgctcgtcgt ccgagtcggt cgccggccgc agctgcggct cgttcgccta cgaatgcctg     660
gccaccaacg gcagcggctg gatcatgatc cgcgacagcg acgtgggcga cctctcggcc     720
gaccactgct accagcgcgt gggcggctgc accggcctgc agagcgtgac cgacagcacc     780
tggcgcaacg gctccaccaa ctggggcctg aaggccaacc tgaactggct caacggcttc     840
gtcacccac                                                             849
```